United States Patent [19]

Hizukuri

[11] Patent Number: 4,593,005
[45] Date of Patent: Jun. 3, 1986

[54] STRAINS OF ASPERGILLUS AND USE THEREOF TO PRODUCE AMYLOLYTIC ENZYMES

[75] Inventor: Susumu Hizukuri, Kagoshima, Japan

[73] Assignee: Daikin Industries, Ltd., Osaka, Japan

[21] Appl. No.: 638,063

[22] Filed: Aug. 6, 1984

[30] Foreign Application Priority Data

Aug. 8, 1983 [JP] Japan .................................. 58-144544

[51] Int. Cl.[4] .......................... C12N 9/30; C12N 1/14; C12P 19/14; C12P 7/14; C12R 1/68
[52] U.S. Cl. ....................................... 435/203; 435/99; 435/162; 435/254; 435/916
[58] Field of Search ................... 435/99, 96, 203, 254, 435/916

[56] References Cited

U.S. PATENT DOCUMENTS 4,316,956 2/1982 Lutzen .................................... 435/96
4,514,496 4/1985 Yoshizumi et al. ................... 435/162

OTHER PUBLICATIONS

American Type Culture Collection Catalogue of Strains I, 15th Edition, 1982, pp. 285, 285.
"Notes on Thermophilic Fungi in Japan", Trans. Mycol. Soc. Japan, 14:144–161 (1973).
Kenneth B. Raper et al., "The Genus Aspergillus", Chapter XIV, pp. 238–269 (1965).

Primary Examiner—Lionel M. Shapiro
Attorney, Agent, or Firm—Birch, Stewart, Kolasch & Birch

[57] ABSTRACT

A novel strain Aspergillus K27 belonging to genus Aspergillus which has the same taxonomical characteristics as those of *Aspergillus fumigatus* except that
(1) its conidiophore is colorless and
(2) its growing temperature range is between 10° and 55° C., which produces amylolytic enzymes which can hydrolyze alpha-amylase resistant starch as well as usual starch.

10 Claims, 3 Drawing Figures

STRAINS OF ASPERGILLUS AND USE THEREOF TO PRODUCE AMYLOLYTIC ENZYMES

FIELD OF THE INVENTION

The present invention relates to novel strains and use thereof. More particularly, it relates to novel strains belonging to genus Aspergillus and preparation of D-glucose from starch by the use of said novel strains. Further, ethanol can be produced from starch in one step without cooking when the enzymes of the invention are used together with a microorganism which produces ethanol from sugars.

BACKGROUND OF THE INVENTION

Enzymatic preparation of D-glucose comprises a step for liquefying starch (liquefaction of gelatinized starch by alpha-amylase) and a step for saccharifying liquefied starch (saccharification of liquefied starch by glucoamylase). As corn starch is increasingly used as a raw material for the production of D-glucose in these days, alpha-amylase resistant starch (hereinafter referred to as "alpha-RS") which is hardly liquefied is troublesomely produced. Since alpha-RS is not hydrolyzed in the subsequent saccharifying step either, it makes filtration of the saccharified liquid difficult. Further, it reduces transparency of the liquid product so that a high quality product is not obtained, and the yield of D-glucose is decreased. Its disposal is also troublesome as it is hardly hydrolyzed.

An enzyme that hydrolyzes alpha-RS has not been known. There are known several methods for hydrolyzing alpha-RS to obtain a transparent product including a two-step method which comprises reheating the liquefied product to a temperature from 120° to 140° C., cooling to about 80° C. and adding a liquefying enzyme to hydrolyze it, and a method comprising gelatinizing starch at a temperature higher than 100° C. and liquefying it to suppress production of alpha-RS. However, the two step method requires a large amount of energy to gelatinize or liquefy starch and further special equipment since gelatinized starch has very high viscosity. On the contrary, in a one step method in which starch is saccharified at a temperature of from 25° to 70° C., the viscosity of the starch solution is low and the steps are simplified.

As a result of extensive study, it has now been found that specific strains belonging to genus Aspergillus produce enzymes which effectively hydrolyze starch including alpha-RS and can be used in the one step method for preparing D-glucose from starch.

SUMMARY OF THE INVENTION

According to one aspect of the present invention, there is provided a novel strain Aspergillus K27 belonging to genus Aspergillus which has the same taxonomical characteristics as those of *Aspergillus fumigatus* except that
(1) its conidiophore is colorless and
(2) its growing temperature range is between 10° and 55° C.

According to another aspect of the invention, there are provided amylolytic enzymes produced by the novel strain of the invention.

DETAILED DESCRIPTIION OF THE INVENTION

Figure 1:
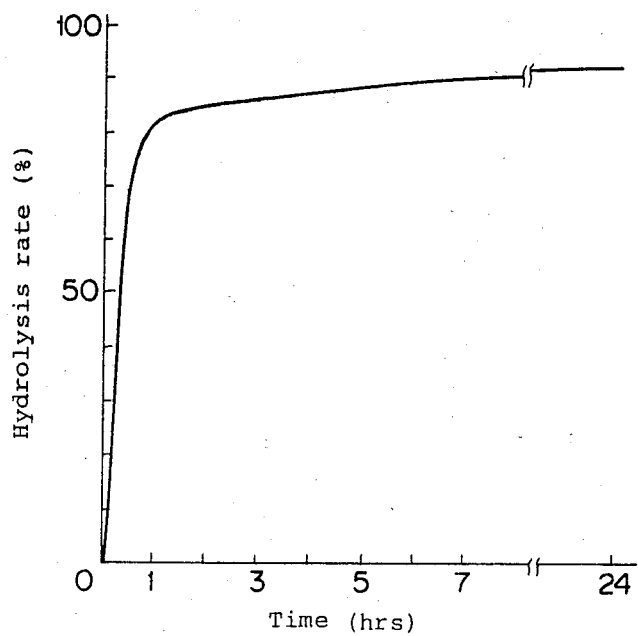
FIGS. 1 and 2 show the hydrolysis curves of alpha-RS and raw corn starch respectively which are obtained in Example 3.

One of the novel strains is Aspergillus K27 AC-1, which is deposited at Fermentation Research Institute, Agency of Industrial Science and Technology in Japan under the Budapest Treaty under the deposition number FERM BP-568.

By cultivating them, the strains of the invention belonging to genus Aspergillus produce amylolytic enzymes which can hydrolyze alpha-RS. With said enzymes, alpha-RS is hydrolyzed at a temperature lower than 100° C., which simplifies the method for producing D-glucose. The enzymes of the invention act on and hydrolyze not only purified starch (eg. corn starch, potato starch, etc.) but also crushed, ground or mashed cereals, potatoes and seeds (eg. corn, rice, wheat, potato, sweet potato, tapioca, cassaba, banana, acorn, etc.) to yield D-glucose. Thus, in addition to the hydrolysis of alpha-RS, the novel strains of the invention can be used for producing D-glucose from various kinds of starch and for treating waste liquid containing starch.

The taxonomical characteristics of Aspergillus K27 AC-1 are as follows:

I. Growing state on various culture mediums (1) Malt extract agar culture medium The strain grows well and after 3 days at 37° C., forms a colony having a diameter of about 50 mm.

The basal hyphae layer is flat and thin. The surface of the colony is velvety or floccose. The color of the colony is initially white and becomes green or dark green as many conidiophores are formed. The underside of the colony is initially colorless but later becomes pale yellow.

(2) Czapek's agar culture medium

The strain grows well and after 3 days at 37° C., forms a colony having a diameter of about 45 mm.

The basal hyphae layer is flat and comparatively thin. The surface of the colony is velvety or floccose. The color of the colony is initially white and becomes green or dark green as many conidiophores are formed. The underside of the colony is initially colorless but later becomes pale yellow.

II. Physiological properties (1) Growing range (on malt extract agar culture medium)
  pH: 3–8
  Temperature: 10°–55° C.
(2) Optimum growing range (on malt extract agar culture medium)
  pH: 4–7
  Temperature: 35°–45° C.

III. Morphological properties

Conidial head:
  Cylindrical
  Length, 120–200 microns
  Diameter, 30–60 microns
  Pale Green Conidiophore:
- Length, 150–200 microns
- Diameter, 2.5–8 microns
- Standing straight by branching from basal or aerial hyphae
- Smooth surface and colorless Terminal vesicle:
- Lageniform
- Diameter, 15–28 microns
- Pale green
- On the upper half, phialides being formed Metula: Not formed Phialide:
- 6.5–9.5 microns × 2–2.5 microns
- Pale green Conidiospore:
- Globose or subglobose
- Diameter, 2.4–3.0 microns
- Rough surface
- Cluster being dark green.

From the above taxonomical characteristics, it is found that the novel strain of the invention belongs to genus Aspergillus. Among strains belonging to genus Aspergillus, *Aspergillus fumigatus* is known as a thermophilic fungus.

The strains of the invention has colorless conidiophore and a growing temperature range between 10° and 55° C., while *Aspergillus fumigatus* has green conidiophore and a growing temperature range between 20° and 50° C. (cf. T. Awao and K. Mitsugi, Trans. Mycol. Soc. Japan, 14, 145 (1973)).

In respect of the color of conidiophore and the growing temperature which are important factors in the classification of mold, the strains of the invention are distinctly different from *Aspergillus fumigatus*. Therefore, the strains of the invention are novel and named Aspergillus K27.

For the production of the amylolytic enzymes by the use of the novel strains of the invention, they are cultivated in a conventional solid or liquid culture medium which is used in the production of amylases. A cultivation temperature is usually from 10° to 55° C., preferably from 35° to 45° C., and pH is from 3 to 8, preferably from 4 to 7. After cultivation for 3 to 7 days, a significant amount of the amylolytic enzymes of the invention is accumulated.

The culture medium contains at least one carbon source (eg. starch, hydrolyzed starch, corn meal, wheat flour, waste malasses, etc.) and at least one nitrogen source (eg. peptone, cotton seed oil dregs, meat extract, yeast extract, casein, corn steep liquor, malt extract, soybean oil, skim milk, inorganic ammonium salts, inorganic nitrates, etc.). Inorganic salts which are essential to the growth of the strains (eg. $KH_2PO_4$, $FeSO_4$, $MgSO_4$, $KCl$, $CaCl_2$, $CoCl_2$, $MnSO_4$, etc.) and optionally organic micronutrients may be added to the culture medium.

The culture medium as such in which the strain of the invention has been cultured may be used as a crude enzyme source. Either the mycelia recovered from the culture medium or the culture filtrate may also be used. Further, 60% ammonium sulfate fraction of the culture filtrate and its 55% isopropanol fraction are used as the enzyme source.

The amylolytic activity of the enzymes produced by the novel strains of the invention may be measured by the following procedures:

An enzyme solution is incubated with 1% soluble starch solution at 45° C., pH 4.5 for 15 minutes, and a total amount of reducing sugars produced is determined by the Somogyi-Nelson method. One unit of the enzymatic activity is defined as an amount of the enzymes that liberates 1 micromole of glucose equivalent per minute under these conditions.

Hydrolysis of starch with the enzymes of the invention is carried out at a temperature of from 25° to 70° C., preferably from 45° to 60° C. at pH of from 3 to 8, preferably from 4 to 6. Hydrolysis may be carried out on standing or preferably with gentle stirring so that starch is homogeneously suspended in the medium. The enzymes to be used is 0.01 to 1.0 unit per milligram of starch. The hydrolysis time varies with other conditions such as temperature, pH, the amount of the enzymes, the kind of starch to be hydrolyzed, etc.

When the amylolytic enzymes of the invention are used together with a microorganism which produces ethanol from sugars, ethanol is produced from not only the purified starch but also the crushed, ground or mashed cereals, potatoes and seeds in one step without cooking. Specific examples of such microorganism are yeast belonging to genus Saccharomyces and bacterium belonging to genus Zymomonas. The temperature and pH in the alcoholic fermentation vary with the kind of the microorganism to be used. Usually, the fermentation temperature is from 25° to 55° C., and pH is from 3.5 to 8.0.

The present invention will be hereinafter explained further in detail by following Examples.

EXAMPLE 1

Separation of strain

Soil collected at Korimoto 1-chome, Kagoshima-shi, Japan was diluted to 1,000 times with sterilized physiological saline. 1 ml of the solution was mixed with 9 ml of the following agar culture medium for separation (I), charged in a sterilized petri dish and cultivated at 45° C. for 2 days.

Agar culture medium for separation (I)

| | |
|---|---|
| $NH_4NO_3$ | 0.1% |
| $MgSO_4.7H_2O$ | 0.02% |
| $KH_2PO_4$ | 0.14% |
| Yeast extract | 0.01% |
| Alpha-RS[1] | 0.5% |
| Agar | 1.5% |
| (pH 6.1–6.3) | |

Note [1]
Obtained by collecting insoluble starch produced during liquefying wheat starch and then freeze-drying it.

A colony formed during the cultivation was inoculated on the following slant agar culture medium (II) and cultivated at 45° C. for 2 days.

Slant agar culture medium (II)

| | |
|---|---|
| Peptone | 0.5% |
| Yeast extract | 0.3% |
| Malt extract | 0.3% |
| D-glucose | 0.2% |
| Agar | 1.5% |
| (pH 7.0) | |

One loop of the conidia of this strain was diluted 10,000 times with physiological saline. 1 ml of the solution was mixed with 9 ml of the agar culture medium for separation (I) and cultivated in a sterilized petri dish at 45° C. for 2 days to form plural colonies. The colonies were identified as the same ones with the naked eyes and a microscope.

Then, 10 colonies were picked up and transferred to 10 tubes with the slant agar culture medium (II) and cultivated individually at 45° C. for 2 days. The colonies grown in each tube were identified as the same kind as each other with the naked eyes and a microscope, and the state on the culture medium and the physiological properties of the colonies grown in each tube were identical to each other and the same as described before.

From these results, each of them was found to be a purely isolated single strain.

Thereafter, a protecting agent (an aqueous solution containing 10% of skim milk and 1% of sodium glutamate) was added on the thus purely grown conidia on the slant agar culture medium to prepare a suspension of spores. 0.2 ml samples of the suspension were poured into ampouls and freeze-dried.

The freeze drying was carried out by slowly cooling to −30° to −40° C., drying at a room temperature at 0.03 Torr. for 18 to 20 hours and sealing the ampoul under vacuum, which was kept at 4° C.

After 3 months, the thus prepared freeze-dried conidia were restored, in which physiological saline was used as a restoring liquid and transferred to a malt extract culture medium. The state on the culture medium and the physiological properties of the strain were the same as those before being freeze-dried.

EXAMPLE 2

Aspergillus K27 AC-1 was cultivated on the slant agar culture medium (II) at 45° C. for 2 days. One loop of the conidia was inoculated on 100 ml of a culture medium having the following composition kept in 500 ml flask and cultivated at 45° C. for 5 days. The culture medium was filtrated and the amylolytic activity of the filtrate was measured to be 12 U/ml.

| Composition | |
|---|---|
| Wheat starch | 2.0% |
| $NH_4NO_3$ | 0.1% |
| Malt extract | 0.01% |
| Corn steep liquor | 0.08% |
| $KH_2PO_4$ | 0.14% |
| $FeSO_4.7H_2O$ | 0.001% |
| $MgSO_4.7H_2O$ | 0.05% |
| KCl | 0.05% |
| (pH 6.1-6.3) | |

EXAMPLE 3

Figure 2:
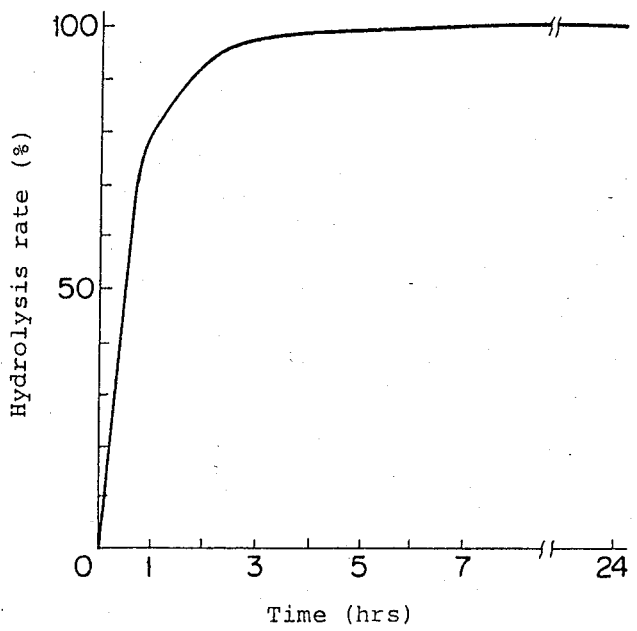

An amount corresponding to the amylolytic activity of 25 units of the filtrate obtained in Example 2 was reacted with 25 mg of alpha-RS or 25 mg of raw corn starch suspended in 5 ml of a buffer (pH 4.5) at 55° C. The total amount of the reducing sugars produced was measured by the Somogyi-Nelson method with the passage of time to calculate hydrolysis rate (total amount of the reducing sugars/total amount of carbohydrates) from which a hydrolysis curve was drawn. FIGS. 1 and 2 shows the hydrolysis curves for alpha-RS and raw corn starch respectively.

Under these conditions, 92% of alpha-RS was hydrolyzed to D-glucose after 24 hours and about 100% of raw corn starch was hydrolyzed to D-glucose after 7 hours.

EXAMPLE 4

25 units of the enzymes obtained in Example 2 was reacted with 250 mg of corn starch suspended in 5 ml of a buffer (pH 4.5) at 55° C. on standing to saccharify the corn starch. The amount of the D-glucose produced was measured by the glucose oxydase-peroxydase method to calculate the saccharification rate. Under these conditions, the saccharification rate was 85% after 24 hours and 95% after 48 hours.

EXAMPLE 5

Figure 3:
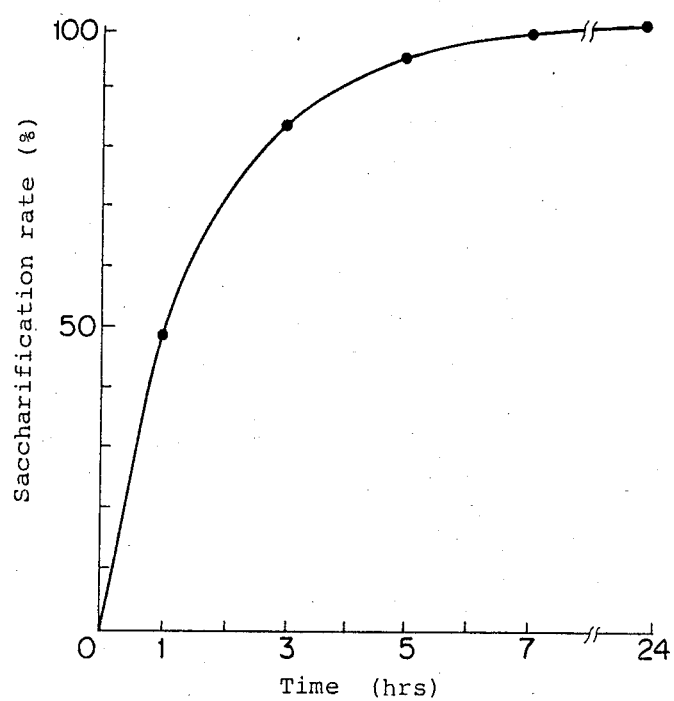
FIG. 3 shows the saccharification rate obtained in Example 5.

In the same manner as in Example 4 but stirring the suspension at 100 rpm, corn starch was saccharified. The saccharification rate was 98% after 7 hours and 100% after 24 hours. These results are shown in FIG. 3.

EXAMPLE 6

20 g of raw corn starch, 400 units of the enzymes obtained in Example 2 and 0.5 g of baker's yeast were charged in a 500 ml fermentation vessel and tap water was added to 80 ml. pH was adjusted to 4.6 to 6.0 and fermentation was carried out at 30° C.

Change with the time passage of the fermentation rate (amount of produced ethanol×100/theoretical amount of ethanol to be produced) was as follows:

| Time (hours) | 24 | 48 | 72 |
|---|---|---|---|
| Rate (%) | 48.7 | 80.1 | 88.3 |

EXAMPLE 7

33 g of ground corn, 1,000 units of the enzymes obtained in Example 2 and 1.0 g of baker's yeast were charged in a 500 ml fermentation vessel and tap water was added to 100 ml. The pH was adjusted to 4.6 to 6.0 and fermentation was carried out at 30° C.

The change with the time passage of the fermentation rate was as follows:

| Time (hours) | 24 | 48 | 72 |
|---|---|---|---|
| Rate (%) | 56.2 | 80.7 | 86.5 |

What is claimed is:

1. A biologically pure culture of Aspergillus K27 AC-1 (FERM BP-568) which has the same taxonomical characteristics as *Aspergillus fumigatus* except that
   (1) its conidiophore is colorless and
   (2) it grows at temperatures of from 10° C. to 55° C.
2. A composition comprising: Aspergillus K27 AC-1 (FERM BP-568); and a sterilized culture medium.
3. The composition of claim 2, wherein said culture medium is an agar culture medium.
4. The composition of claim 2, which further includes an ethanol producing microorganism.
5. The composition of claim 3, wherein said ethanol producing microorganism is a yeast belonging to the genus Saccharomyces.
6. The composition of claim 3, wherein said ethanol producing microorganism is a bacterium belonging to the genus Zymomonas.
7. A freeze dried culture of Aspergillus K27 AC-1 (FERM BP-568).

8. An Aspergillus culture capable of producing amylolytic enzymes consisting essentially of a novel strain Aspergillus K27 AC-1 (FERM BP-568).

9. A process for producing amylolytic enzymes which comprises cultivating in a culture medium a novel strain of Aspergillus K27 AC-1 (FERM BP-568) which has the same taxonomical characteristics as *Aspergillus fumigatus* except that
   (1) its conidiophore is colorless and
   (2) it grows at temperatures of from 10° C. to 55° C. to produce said amylolytic enzymes.

10. The process of claim 9, which further comprises the steps of purifying said amylolytic enzymes.